(12) United States Patent
Hagn

(10) Patent No.: US 8,678,009 B2
(45) Date of Patent: Mar. 25, 2014

(54) STERILE COVER SYSTEM FOR STERILELY COVERING A MEDICAL TECHNICAL ROBOT ARM AND METHOD FOR STERILELY COVERING A MEDICAL TECHNICAL ROBOT ARM

(75) Inventor: Ulrich Hagn, München (DE)

(73) Assignee: Deutsches Zentrum fur Lurft-und Raumfahrt E.V, Cologne (DE)

( * ) Notice: Subject to any disclaimer, the term of this patent is extended or adjusted under 35 U.S.C. 154(b) by 196 days.

(21) Appl. No.: 13/266,691

(22) PCT Filed: Apr. 20, 2010

(86) PCT No.: PCT/EP2010/055193
§ 371 (c)(1),
(2), (4) Date: Oct. 27, 2011

(87) PCT Pub. No.: WO2010/127940
PCT Pub. Date: Nov. 11, 2010

(65) Prior Publication Data
US 2012/0045598 A1    Feb. 23, 2012

(30) Foreign Application Priority Data

May 5, 2009    (DE) .......................... 10 2009 019 695

(51) Int. Cl.
*A61B 19/08* (2006.01)
*A61B 19/00* (2006.01)
*A61B 1/04* (2006.01)

(52) U.S. Cl.
USPC ............................ 128/852; 606/130; 600/133

(58) Field of Classification Search
USPC .......... 128/852, 849, 846, 856; 606/129, 130; 600/101, 102, 121–125, 133; 901/49–50; 74/490.01
See application file for complete search history.

(56) References Cited

U.S. PATENT DOCUMENTS 5,368,545 A * 11/1994 Schaller et al. ................. 600/37
5,790,307 A    8/1998 Luber et al.
(Continued)

FOREIGN PATENT DOCUMENTS

WO    9220295 A1    11/1992

OTHER PUBLICATIONS

International Search Report dated Jun. 25, 2010 from corresponding International Patent Application No. PCT/EP2010/055193-3 pages.

*Primary Examiner* — Patricia Bianco
*Assistant Examiner* — Tarla Patel
(74) *Attorney, Agent, or Firm* — Maier & Maier, PLLC

(57) ABSTRACT

The sterile cover system for sterilely covering a medical technical robot arm with a connecting element, having a receiving bore with an inner wall, for endoscopic devices, is provided with a sack-shaped drape for enclosing the connecting element. The drape comprises a film tube which is adapted to the receiving bore for covering the inner wall, and a guiding element which is removably attached to a first end of the film tube, adapted to the receiving bore and extends into the film tube in an initial state of the sterile cover system. The film tube can be inserted into and guided through the receiving bore by means of the guiding element such that a surface of the film tube, facing inward in an initial state of the sterile cover system, faces the inner wall of the receiving bore in a state in which the film tube is guided through the receiving bore.

22 Claims, 3 Drawing Sheets

(56) References Cited

U.S. PATENT DOCUMENTS

Figure 1:
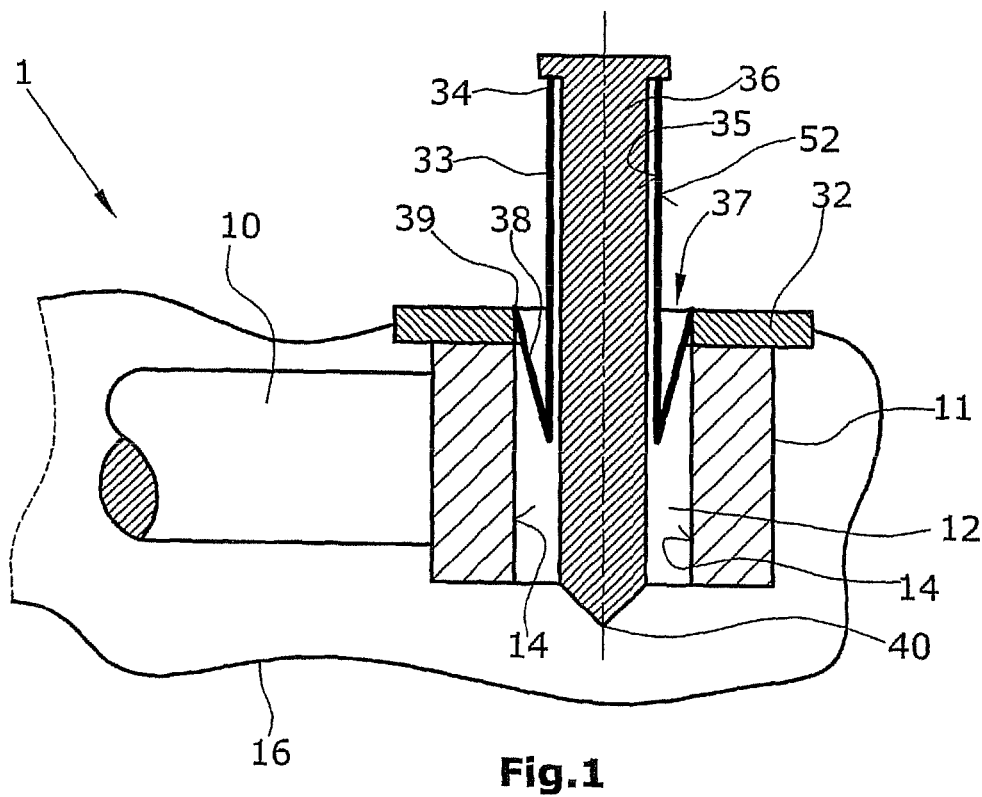

| | | |
|---|---|---|
| 6,852,077 B2 * | 2/2005 | Ouchi et al. .................. 600/122 |
| 8,445,093 B2 * | 5/2013 | Lemer ........................... 428/131 |
| 2002/0091374 A1 | 7/2002 | Cooper |
| 2004/0049205 A1 | 3/2004 | Lee et al. |
| 2004/0103904 A1 * | 6/2004 | Auerbach et al. ............. 128/856 |

* cited by examiner

STERILE COVER SYSTEM FOR STERILELY COVERING A MEDICAL TECHNICAL ROBOT ARM AND METHOD FOR STERILELY COVERING A MEDICAL TECHNICAL ROBOT ARM

RELATED APPLICATIONS

This is the U.S. national stage application which claims priority under 35 U.S.C. §371 to International Patent Application No.: PCT/EP2010/055193 filed on Apr. 20, 2010, which claims priority to German Patent Application No. 10 2009 019 695.1 filed on May 5, 2009, the disclosures of which are incorporated by reference herein their entireties.

The invention relates to a sterile cover system for sterilely covering a medical technical robot arm according to the pre-characterizing part of claim 1, and a method for sterilely covering a medical technical robot arm.

In the field of surgery, the surfaces of instruments provided for contact with the patient or with the interior of the patient' body have to be sterile, i.e. free of living microorganisms. For sterilization of apparatus, various methods exist. To be counted among these methods are e.g. steam sterilization, hot-air sterilization, fractional sterilization, chemical sterilization, radiation sterilization or plasma sterilization. In most cases, sterilization is already performed externally of the operating theater so that the apparatus will be placed therein while being in a sterile state. In some apparatus, however, their technical design or their size makes it impossible for them to be sterilized. For instance, medical robots, as are nowadays frequently used in surgery, comprise electronic components which could suffer damage when subjected to conventional sterilization methods.

In order to avoid that non-sterile surfaces of medical robots could contaminate the sterilized apparatus or instruments, medical robots will be provided with a sterile packing, which usually is done in situ.

As a sterile packing for the above apparatus such as, e.g., medical robots, use is mostly made of sterile packing materials such as films, also referred to as drapes. Generally, a drape is a sterilized film tube which will be pulled over the technical apparatus and be fixed thereon. In this regard, it is especially important that the drape, while being applied, will not be damaged and that the sterile surface of the drape facing toward the sterile side of the operational field will not be contaminated.

In the field of endoscopic robot-supported surgery, use is made of robotic instruments which are guided by a robot arm. Instruments of this type comprise a rod-shaped element provided with a functional end portion, e.g. in the form of tongues or scissors. Said functional end will get into direct contact with the interior of the patient's body and thus has to be sterile. In a robot system as described e.g. in DE 10 2004 054 866 B3, the instrument is coupled to the robot system in such a manner that the instrument will be advanced through a hollow shaft of the robot with the instrument's functional end which is oriented forward. Contact between the inner wall of the hollow shaft and the functional end of the instrument may thus happen to cause contamination of the functional end.

However, sterilizing a hollow shaft of a robot arm is possible only with very high technical expenditure or not at all. Even though known sterile packings in the form of drapes can cover the robot arm in a sterile manner, this form of covering the hollow shaft will entail the problem that a drape pulled through the hollow shaft may develop creases and that the film surfaces located in the subsequently sterile region may become contaminated during the pull-through movement.

Thus, it is an object of the present invention to provide a sterile cover system for sterilely covering a medical technical robot arm comprising a connecting element for endoscopic devices, said connecting element having a receiving bore, wherein said system, while avoiding the above mentioned disadvantages, shall allow for a reliable sterile covering, particularly of the connecting element.

A further object of the invention resides in providing a method for reliably covering a medical technical robot arm in a sterile manner by use of a connecting element for endoscopic devices, the connecting element being provided with a receiving bore.

The above objects are achieved by the features defined in claims 1 and 16.

The sterile cover system according to the invention, provided for sterilely covering a medical technical robot arm comprising a connecting element for endoscopic devices, said connecting element having a receiving bore with an inner wall, comprises a sack-shaped drape for enclosing the connecting element, and a film tube adapted to the receiving bore for covering the inner wall. Fastened to the first end of the film tube is a removable guiding element, said guiding element being adapted to the receiving bore and extending into the film tube in the initial state of the sterile cover system. The film tube can be inserted into the receiving bore and passed therethrough together with the guiding element, in such a manner that a surface of the film tube facing inward in the initial state of the sterile cover system will be facing toward the inner wall of the receiving bore in the state of the film tube when the latter has been passed through the receiving bore.

With the aid of the guiding element, there is rendered possible an exact guidance of the film tube through the receiving bore of the connecting element for endoscopic devices, thus avoiding creases in the film tube. By use of the guiding element which in the initial state extends into the film tube, it is made possible to insert the film tube into, and pass it through, the receiving bore in such a manner that the film tube will be turned inside out during the insertion and pass-through movement. During the insertion and pass-through movement of the film tube through the receiving bore, the surface of the film tube does not perform a sliding movement but a rolling movement. In this manner, contamination of further surfaces of the film tube is prevented, and it is safeguarded that the surface which in the passed-through state of the film tube is facing inward, i.e. away from the receiving bore—which surface during the later passage of an endoscopic device through the receiving bore may happen to contact the endoscopic device—does not have a chance to get into contact with the inner wall of the connecting element or some other part of the robot arm. Thus, there is guaranteed a reliable sterile covering of the inner wall of the receiving bore and of the connecting element for endoscopic devices.

Apart from the above effects, the film tube can be handled and respectively guided in an advantageous manner with the aid of the guiding element.

It can be provided that the guiding element is rod-shaped, it being preferred that a free end of the guiding element is provided with a pointed tip which preferably is suited for piercing the drape. Due to the rod-shaped design of the guiding element, the guiding element can be conveniently passed through the receiving bore of the connecting element. The pointed tip at a free end of the guiding element of the drape makes it possible e.g. that conventional drapes can be used in the sterile cover system because, prior to passing the film tube through the receiving bore with the aid of the guiding element, the drape can be pierced at a corresponding site for inserting the foil tube into the interior of the drape and into the receiving bore. Further, after the film tube has been passed through the receiving bore, the tip can be used to pierce the drape abutting the other end of the connecting element. Further still, the pointed tip on a free end of the guiding element allows for convenient insertion of the guiding element into the receiving bore.

According to a particularly preferred embodiment, it is provided that the sack-shaped drape comprises at least one opening having a surrounding edge and being adapted to the guiding element and/or the receiving bore, said opening allowing the guiding element and the film tube to be at least partly passed therethrough. By the provision of a first opening on the sack-shaped drape, passing the guiding element and the film tube through the receiving bore will be facilitated since there is no need to form an opening in the sack-shaped drape by use of the guiding element.

Further, with the aid of the first opening, the drape can be precisely positioned on the connecting element in that the opening is arranged in the region of the receiving bore.

It can be provided that the film tube can be fastened or is fastened by a second end thereof to the surrounding edge. In this manner, the process of passing the film tube through the receiving bore is facilitated since, by fastening the second end of the film tube to the surrounding edge of the first opening, there is avoided the risk that the film tube, when being passed through the receiving bore, could slide all the way through in an uncontrolled manner.

According to one embodiment of the invention, it is provided that a first plate with a throughgoing bore formed therein is arranged on the drape, said throughgoing hole forming the first opening. With the aid of first plate having a throughgoing hole, the drape can be positioned in an advantageous manner on the connecting element. Further, the first plate advantageously makes it possible to fasten the film tube to the first opening.

It can be provided that the film tube is by its second end tightly connected to the plate. In this manner, it is not only guaranteed that the film tube cannot slide all the way through when passing through the receiving opening but, moreover, it is also made possible that the film tube and the drape can be fastened to the connecting element as one unit.

According to an alternative embodiment, it is provided that the film tube can be connected by its second end to the plate mechanically or by a bonding connection. Thus, prior to being inserted into the receiving opening and being passed therethrough, the film tube will be connected to the drape via the first plate, thereby preventing the film tube from sliding all the way through.

According to a preferred embodiment, it is provided that the film tube is made of an elastic material, preferably silicone. By providing a film tube of elastic material, it is prevented that the film tube can develop creases when being passed into the receiving bore. Since silicone can be sterilized in an advantageous manner, this material has proven to be of particular advantage for a film tube of the invention.

The drape according to the invention can comprise at least one second opening having a surrounding edge and being adapted to the guiding element and/or the receiving bore, said opening allowing the guiding element and the film tube to be passed at least partly therethrough. With the aid of the second opening, the drape can be advantageously positioned on the connecting element, and the guiding element and the first end of the film tube, once they have been passed through the receiving opening, can be passed through the drape.

In this regard, it can be provided that the film tube can be fastened by its first end to the surrounding edge of the second opening. Thereby, it is rendered possible that, after passing the film tube through the receiving bore, the film tube and the sack-shaped drape will form a tightly connected unit so that all of the surfaces of the connecting element facing toward the ambience will be covered either by the drape or by the film tube.

On the drape, a second plate with a throughgoing opening can be arranged, where the throughgoing opening of said second plate forms the second opening. By said plate with a throughgoing opening, the drape can be advantageously positioned on the connecting element.

Further, also the attachment of the first end of the film tube to the surrounding edge of the second opening can be realized in an advantageous manner with the aid of the second plate.

It can be provided that the film tube can be connected by its first end to the second plate mechanically or by a material connection.

According to a particularly preferred embodiment, it is provided that the first and/or the second plate can be fixed to the connecting element, preferably mechanically, magnetically or by material connection. In this manner, apart from a more precise positioning of the drape to the connecting element, it is also made possible at the same time to fasten the drape to the connecting element with the aid of the first and/or second plate. Apart from this, it is also prevented that the drape could slide out of position while the film tube is being passed through the receiving bore of the connecting element.

According to one embodiment of the sterile cover system of the invention, it is provided that the first and/or the second plate comprises a clamping element for attachment of the respective film tube, said clamping element being preferably plate-shaped. The mechanical attachment of the first end of the film tube to the second plate and/or of the second end of the film tube to the first plate by use of a clamping element makes it possible to fasten the respective ends of the film tube to one of the plates in a simple and quick manner.

The first and/or the second plate and/or the clamping element can have various shapes. For instance, these elements can have an annular shape.

In this arrangement, the clamping element can be connected respectively via a snap- or screw-type connection with the first and/or second plate for generating a clamping force.

The invention further provides a method for sterilely covering a medical technical robot arm comprising a connecting element for endoscopic devices, said connecting element having a receiving bore with an inner wall, wherein said method comprises the following steps:
a) enclosing the robot arm with a sack-shaped drape,
b) introducing a film tube into a first opening in the sack-shaped drape and into the receiving bore with the aid of a guiding element attached to a first end of the film tube,
c) passing the film tube through the receiving bore with the aid of the guiding element in such a manner that that the surface of the film tube facing inward in the initial state of the film tube is facing toward the inner wall of the receiving bore in the state wherein the film tube has been passed through the receiving bore,
d) passing the film tube through a second opening in the sack-shaped drape,
e) detaching the guiding element from the first end of the film tube,
f) fastening the first end of the film tube to the sack-shaped drape in the region of the second opening.

The method according to the invention allows for a reliable sterile covering of a medical technical robot arm comprising a connecting element—having a receiving bore—for endoscopic devices, since, when passing the film tube through the receiving bore, it is guaranteed that those surfaces of the film tube which later are to come into contact with the endoscopic device cannot be contaminated by non-sterile surfaces of the connecting element. This is safeguarded in that the film tube during its passage through the receiving bore will be turned inside out. In the process, the surface of the film tube will not perform a sliding movement but a rolling movement on the surface of the receiving bore, whereby a contamination of other regions of the film tube will be avoided.

According to the method of the invention, it can be provided that, in the initial state of the drape, the first opening is arranged in the sack-shaped drape, the first opening being adapted to the guiding element or the receiving bore.

The arrangement of the first opening in the sack-shaped drape makes it possible to position the drape on the connecting element in an advantageous manner.

In this regard, it can be provided that, in the initial state of the drape, the film tube is by its second end fastened in the region of the first opening of the sack-shaped drape.

By the fact that, in the initial state of the drape, the film tube has already been fastened by its second end to the sack-shaped drape, it is prevented that, when passing the film tube through the receiving bore, the film tube can slide all the way through the receiving bore. As a further benefit, a further method step of fastening the second end to the region of the first opening is avoided.

It can be provided that, in the initial state of the drape, the second opening is arranged on the sack-shaped drape, the second opening being adapted to the guiding element and/or the receiving bore.

According to an alternative exemplary embodiment, it can be provided that the following intermediate step is performed between said steps a) and b):

a1) perforating the sack-shaped drape with the aid of the guiding element for forming the first opening in the sack-shaped drape.

Further, it can be provided that the following intermediate step is performed between said steps c) and d):

c1) perforating the sack-shaped drape with the aid of the guiding element for forming the second opening in the sack-shaped drape.

By the provision of the additional intermediate steps a1) and/or c1), wherein the first and respectively the second opening in the sack-shaped drape are formed by piercing the sack-shaped drape with the aid of the guiding element, the sack-shaped drape employed in the method of the invention can be used on different connecting elements. Only after the robot arm has been covered by a sack-shaped drape of the invention, the required openings will be formed at the corresponding positions in the drape with the aid of said two method steps.

The method of the invention can further comprise the following intermediate step performed between said steps a) and b):

a2) fastening a second end of the film tube to the sack-shaped drape in the region of the first opening.

By the provision of this step, it is prevented that, in case of a drape wherein the film tube in the initial state is not connected to the drape, the film tube could slide all the way through the receiving bore.

Figure 2:
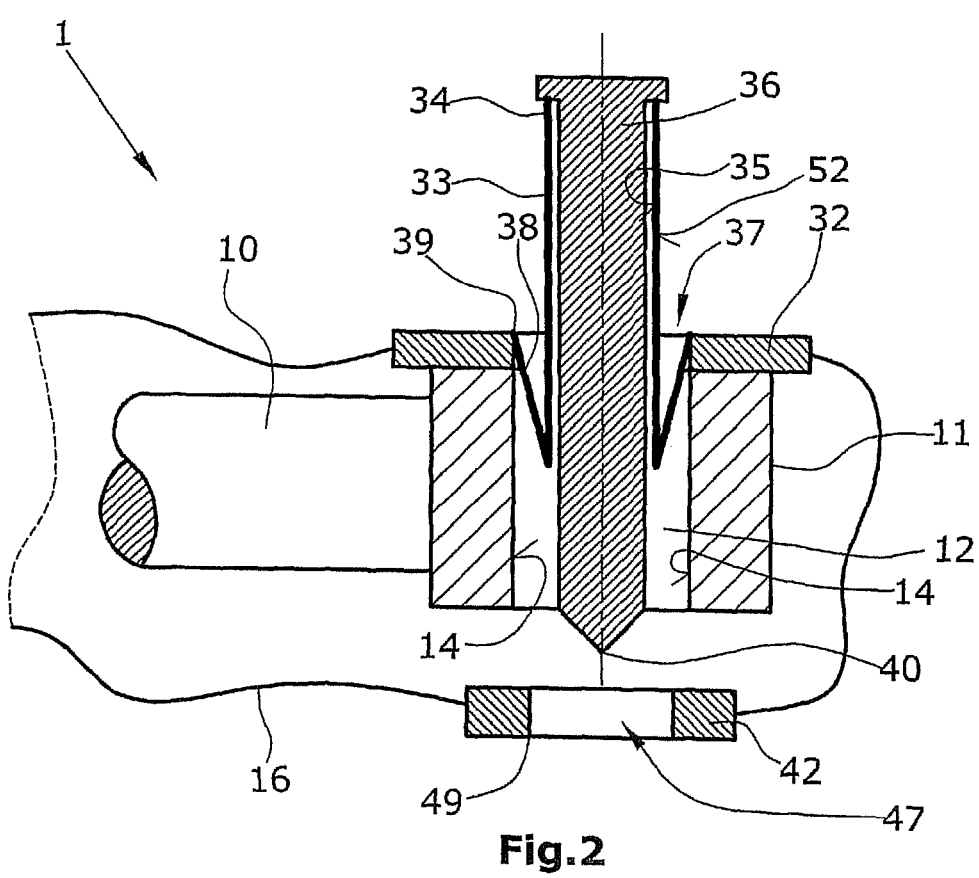
Figure 3:
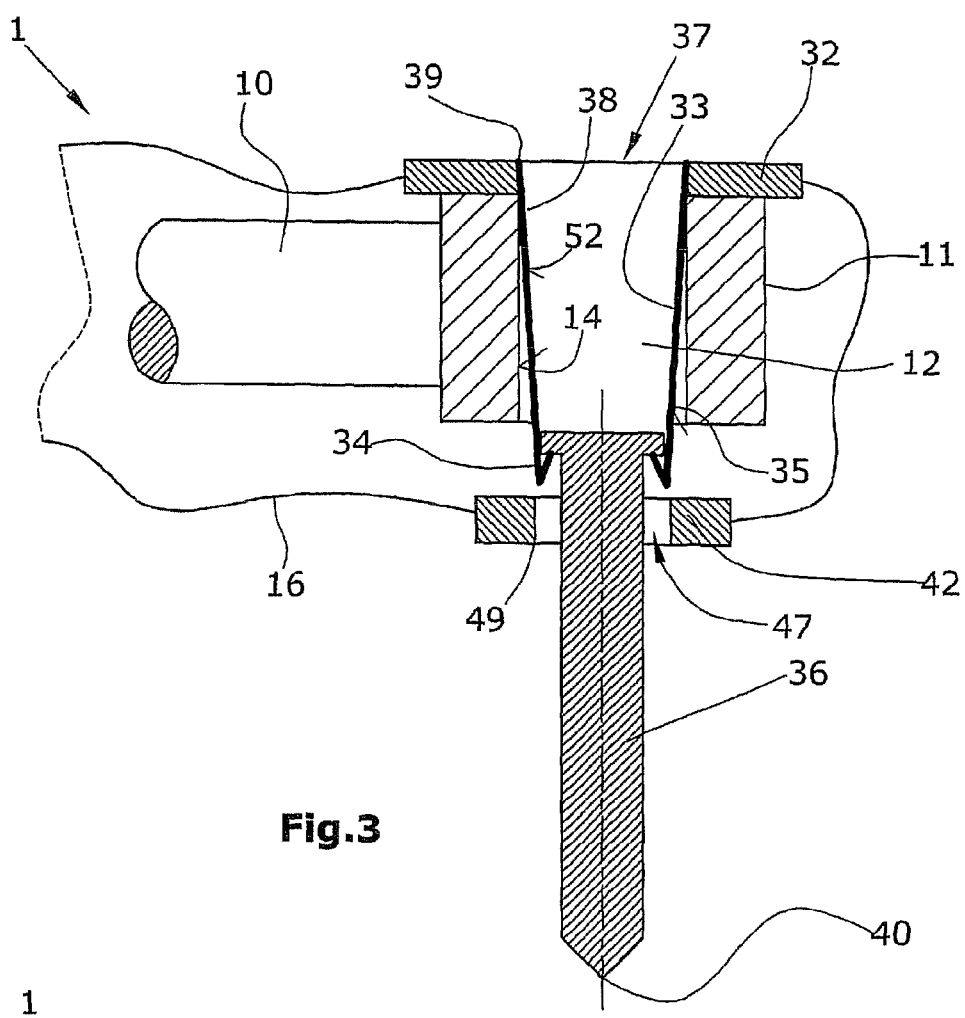
Figure 4:
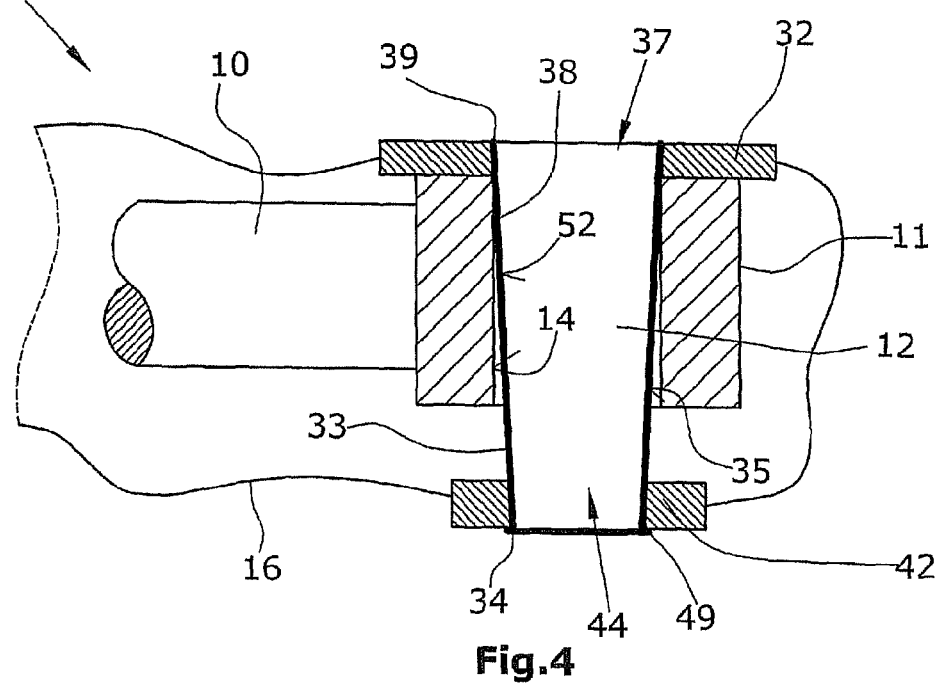
Figure 5:
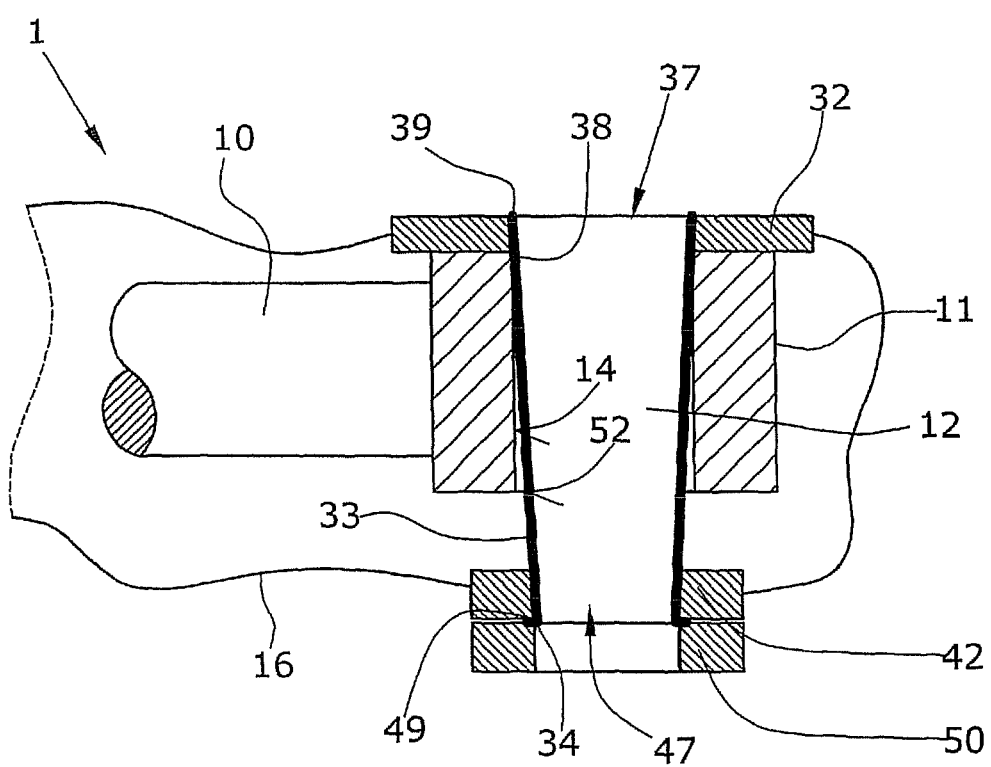

The invention will be explained in greater detail hereunder with reference to the accompanying drawings. Therein, the following is shown:

FIG. 1 is a sectional view of a first exemplary embodiment of a sterile cover system of the invention, FIGS. 2-4 are schematic sectional views of a second exemplary embodiment of a sterile cover system of the invention in various positions while performing the method of the invention, FIG. 5 is a schematic sectional views of a third exemplary embodiment of a sterile cover system of the invention.

In FIG. 1, there is shown a schematic sectional view of a first exemplary embodiment of a cover system 1 according to the invention. The cover system 1 of the invention is designed for sterilely covering a medical technical robot arm 10 comprising a connecting element 11 for endoscopic devices, said connecting element having a receiving bore 12 with an inner wall 14.

A sack-shaped drape 16 encloses the connecting element 11 and a part or the entirety of the robot arm 10.

Embedded into said drape 16 is a first plate 32 having a throughgoing hole, said throughgoing hole forming a first opening 37 in drape 16.

With the aid of said first plate 32, said sack-shaped drape 16 can be positioned in an advantageous manner on the medical technical robot arm 10 by placing the first plate 32 onto said connecting element 11 in such a manner that the first opening 37 will be in alignment with said receiving bore 12. In the process, the sack-shaped drape 16 can be fastened to the medical technical robot arm 10 with the aid of the first plate 32 by attaching the first plate 32 mechanically, magnetically or by material connection.

The sterile cover system 1 further comprises a film tube 33 adapted to the receiving bore 12, which film tube is suited for covering said inner wall 14 of receiving bore 12. At a first end 34 of film tube 33, a guiding element 36 is removably attached to film tube 33. In the context of the invention, the term "removably attached" is to be understood also in the sense of mechanical and bonding connections of two elements, inclusive of connections which are releasable in an irreversible manner, such as e.g. a welding connection which can be severed only by being cut apart.

The film tube 33 is fastened by its second end 35 to the surrounding edge 39 of the first opening 37.

In the initial state of the sterile cover system 1, the guiding element 36 extends into film tube 33. Guiding element 36 is of such a design that, with the aid of guiding element 36, the film tube 33 can be at least partly introduced into, and passed through, the receiving bore. In the initial state of the sterile cover system 1, an inwardly facing surface 35 of film tube 33 is facing toward guiding element 36.

During the insertion and pass-through movement of guiding element 36 and film tube 33 through receiving bore 12, the film tube 33 will be turned inside out so that the previously inwardly facing surface 35 of film tube 33 will be facing toward the inner wall 14 of receiving bore 12 in the state where the film tube 33 has been passed through receiving bore 12. In the process, the surface 35 of film tube 33 is performing a rolling movement on the inner wall 14 of receiving bore 12 so that a mere little or no sliding movement will take place between the surfaces, thus reducing the danger that other regions of the surfaces of film tube 33 could be contaminated by the receiving bore 12. Particularly, by this approach, the surface 52 of the film tube 33 which in the passed-through state of film tube 33 is facing inward and may directly contact an endoscopic device, cannot come into contact with the non-sterile inner wall 14 of receiving bore 12 and thus cannot be contaminated.

Guiding element 36 is rod-shaped and on a free end thereof comprises a pointed tip 40. Tip 40 does not only facilitate the insertion of the guiding element into the receiving bore but also makes it possible to pierce the part of the drape arranged below the receiving bore 12 for thus forming a second opening through which the film tube 33, after having been passed through the receiving bore 12, can be partly guided out from drape 16.

Thereafter, the guiding element 36 can be removed from film tube 33, and the first end 34 of film tube 33 can be fastened to the drape 16 e.g. by bonding. In this manner, all surfaces of robot arm 10 are covered by sterile material.

In FIGS. 2 to 4, a schematic representation of a second exemplary embodiment of a sterile cover system of the invention is shown in different positions in the performing of the method of the invention. The sterile cover system 1 is different from the sterile cover system of FIG. 1 only in that the drape 16 comprises, opposite to the first plate 32, a second plate 42 having a second opening 47 with a surrounding edge 49.

The sack-shaped drape 16 of the sterile cover system 1, on which there is arranged a film tube 33 having a guiding element 36 fastened on a first end 34, will first be put over a medical technical robot arm 10 comprising a connecting element 11 with a receiving bore 12. The drape 16 has arranged therein a first plate 32 comprising a throughgoing hole forming a first opening 37 in the sack-shaped drape.

With the aid of plate 32, drape 16 can be arranged in an advantageous manner on connecting element 11 so that the first opening 37 will be aligned with the receiving bore 12. In this arrangement, the film tube 33 with the guiding element 36 is located outside of drape 16, with guiding element 36 extending into film tube 33. Drape 16 will be fastened to the medical technical robot arm 10. For this purpose, use can be made e.g. of the first plate 32 by which the drape 16 can be fixed to the connecting element 11 of robot arm 10 mechanically, magnetically or by material connection, e.g. by bonding. Now, with the aid of the guiding element 36, the film tube 33 will be inserted into the receiving bore 12 and, as shown in FIG. 3, be passed through receiving bore 12.

Since the film tube 33 is by its second end 38 fastened to the surrounding edge 39 of the first opening 37, the film tube 33 will be turned inside out while being inserted into and passed through the receiving bore 12, it being prevented at the same time that the film tube 33 could slide all the way through the receiving bore 12 during its insertion and pass-through movement into and respectively through the receiving bore 12.

During the insertion and pass-through movement of the film tube 33 into and respectively through the receiving bore 12, the surface 35 which in the initial state of film tube 33 is facing inward and toward the guiding element 36, will carry out a rolling movement on the inner wall 14 of receiving bore 12, so that there will occur no or only a slight sliding movement between the surface of connecting element 11 and film tube 33. Thereby, it is prevented that the other surfaces of film tube 33, except for the surface 35 of film tube 33 which in the initial state is facing inward, can come into contact with surfaces of connecting element 11. Contamination of these surfaces of film tube 33 is thus avoided. Particularly, by this way of proceeding, the surface 52 of film tube 33 which in the passed-through state of film tube 33 is facing inward and can get into direct contact with an endoscopic instrument, cannot be contaminated by the non-sterile inner wall 14 of receiving bore 12.

As can be seen from FIGS. 3 and 4, the guiding element 36, after having been passed through receiving bore 12, will be passed together with a part of film tube 33 through the second opening 47 of the second plate 42 so that the guiding element 36 and a part of the film tube 33 which comprises the first end 34 of film tube 33 will be arranged outside of drape 16. The guiding element 36 will now be removed from film tube 33, e.g. by cutting it off.

Now, as evident from FIG. 4, the first end 34 of film tube 33 which meanwhile is a free end, will be fastened to the surrounding edge 49 of the second plate 42. This can be performed mechanically or by material connection, e.g. by bonding.

By application of the inventive method for sterilely covering the medical technical robot arm 10, it has now been achieved that all surfaces, inclusive of the inner wall of the receiving bore of connecting element 11, have been reliably covered in a sterile manner. When fastening the endoscopic device to the connecting element 11, the endoscopic device cannot come into contact with the connecting element 11, thus precluding contamination of the endoscopic device.

In FIG. 5, a further exemplary embodiment of a sterile cover system 1 of the invention is shown in schematic sectional view. In FIG. 5, the sterile cover system 1 is represented in the state of attachment to the medical technical robot arm 10.

Thus, the view shown in FIG. 5 substantially corresponds to the view of FIG. 4 depicting the second exemplary embodiment. The exemplary embodiment shown in FIG. 5 differs from the embodiment shown in FIG. 4 by the provision of a clamping element 50 which, for fastening the first end 34 of film tube 33 to the surrounding edge 49 of the second plate 42, is mechanically connected to the second plate 42.

Said clamping element 50 can be fastened e.g. by a snap-on or screw connection to the second plate. In this manner, a particularly stable attachment of the first end 34 to the second opening 47 of drape 16 is possible.

In a sterile cover system 1 of the invention, the film tube 33 can be made of an elastic plastic, e.g. silicone. The elastic nature of film tube 33 has the advantage that, while the film tube 33 is being passed through the receiving bore 12, no or merely slight formation of creases will occur in film tube 33.

The film tube does not necessarily have to be already fastened to the drape. Of course, the drape and the film tube can also be provided as separate parts, with the second end of the film tube being fastened to the first opening in the drape prior to being passed through the receiving bore. This can be performed e.g. by a further clamping element which is fastened to the first plate.

The drape does not necessarily have to comprise plates with the corresponding throughgoing bores for the openings; instead, it is also possible to arrange the openings directly in the drape, i.e. without corresponding plates, or to supply the drape without openings while the corresponding openings can be pierced into the drape with the aid of the guiding element.

Also, it is possible to fasten the drape to the connecting element using both the first plate and the second plate.

The sterile cover system is suited for any kind of medical technical robot arm comprising a connecting element for endoscopic devices which has a receiving bore for the endoscopic devices. The connecting element with receiving bore can also be a hollow shaft, for instance.

The invention claimed is:
1. A sterile cover system for sterilely covering a medical technical robot arm comprising a connecting element for endoscopic devices, said connecting element having a receiving bore with an inner wall, said cover system comprising
 a sack-shaped drape for enclosing the connecting element,
 a film tube capable of being inserted into the receiving bore for covering the inner wall, and a removable guiding element attached to a first end of the film tube, said guiding element extending into the film tube in an initial state of the sterile cover system, the film tube capable of being inserted into and guided through the receiving bore by means of the guiding element in such a manner that a surface of the film tube, facing inward in an initial state of the sterile cover system, faces toward the inner wall of the receiving bore in a state in which the film tube has been guided through the receiving bore.

2. The sterile cover system according to claim 1, wherein the guiding element is rod-shaped, a free end of the guiding element being preferably provided with a tip preferably suited for piercing the drape.

3. The sterile cover system according to claim 1, wherein the sack-shaped drape comprises at least one first opening having a surrounding edge, said opening allowing the guiding element and the film tube to be at least partly passed therethrough.

4. The sterile cover system according to claim 3, wherein the film tube is fastened is fastenable by a second end thereof to the surrounding edge of the first opening.

5. The sterile cover system according to claim 3, wherein a first plate with a throughgoing opening formed therein is arranged on the drape, said throughgoing hole forming the first opening.

6. The sterile cover system according to claim 5, wherein the film tube is by its second end tightly connected to the first plate.

7. The sterile cover system according to claim 5, wherein the film tube can be connected by its second end to the first plate mechanically or by a bonding connection.

8. The sterile cover system according to claim 5 wherein, at least one of the first and the second plate can be fixed to the connecting element, preferably mechanically, magnetically or by material connection.

9. The sterile cover system according to claim 5, wherein at least one of the first and the second plate comprises a clamping element for attachment of the respective end of the film tube, said clamping element being preferably plate-shaped.

10. The sterile cover system according to claim 9, wherein a clamping element can be connected respectively via a snap or screw-type connection with at least one of the first and second plate for generating a clamping force.

11. The sterile cover system according to claim 3, wherein the sack-shaped drape comprises at least one second opening having a surrounding edge, said opening allowing the guiding element and the film tube to be passed at least partly therethrough.

12. The sterile cover system according to claim 11, wherein the film tube can be fastened by its first end to the surrounding edge of the second opening.

13. The sterile cover system according to claim 11, wherein a second plate with a throughgoing opening is arranged on the drape, the throughgoing opening of said second plate forming the second opening.

14. The sterile cover system according to claim 13, wherein the film tube can be connected by its first end to the second plate mechanically or by a bonding connection.

15. The sterile cover system according to claim 1, wherein the film tube is made of an elastic material, preferably silicone.

16. A method for sterilely covering a medical technical robot arm comprising a connecting element for endoscopic devices, said connecting element having a receiving bore with an inner wall, said method comprising the following steps:
a) enclosing the robot arm with a sack-shaped drape,
b) introducing a film tube into a first opening in the sack-shaped drape and into the receiving bore with the aid of a guiding element attached to a first end of the film tube,
c) passing the film tube through the receiving bore with the aid of the guiding element in such a manner that that the surface of the film tube facing inward in the initial state of the film tube is facing toward the inner wall of the receiving bore in the state wherein the film tube has been passed through the receiving bore,
d) passing the film tube through a second opening in the sack-shaped drape,
e) detaching the guiding element from the first end of the film tube,
f) fastening the first end of the film tube to the sack-shaped drape in the region of the second opening.

17. The method according to claim 16, wherein in the initial state of the drape, the first opening is arranged in the sack-shaped drape.

18. The method according to claim 17, wherein in the initial state of the drape, the film tube is by its second end fastened in the region of the first opening of the sack-shaped drape.

19. The method according to claim 16, wherein in the initial state of the drape, the second opening is arranged in the sack-shaped drape.

20. The method according to claim 16, wherein the following intermediate step is performed between said steps a) and b):
a1) perforating the sack-shaped drape with the aid of the guiding element for forming the first opening in the sack-shaped drape.

21. The method according to claim 16, wherein the following intermediate step is performed between said steps c) and d):
c1) perforating the sack-shaped drape with the aid of the guiding element for forming the second opening in the sack-shaped drape.

22. The method according to claim 16, wherein the following intermediate step is performed between said steps a) and b):
a2) fastening a second end of the film tube to the sack-shaped drape in the region of the first opening.

* * * * *

UNITED STATES PATENT AND TRADEMARK OFFICE
CERTIFICATE OF CORRECTION

PATENT NO. : 8,678,009 B2
APPLICATION NO. : 13/266691
DATED : March 25, 2014
INVENTOR(S) : Ulrich Hagn Page 1 of 1

It is certified that error appears in the above-identified patent and that said Letters Patent is hereby corrected as shown below:

On the Title Page, (73), replace "Assignee: Deutsches Zentrum fur Lurft-und Raumfarhrt E.V, Cologne (DE)" with --Assignee: Deutsches Zentrum für Luft- und Raumfahrt e.V.--

Signed and Sealed this
Twenty-sixth Day of May, 2015

Michelle K. Lee
*Director of the United States Patent and Trademark Office*